(12) United States Patent
Schiraldi et al.

(10) Patent No.: US 6,204,386 B1
(45) Date of Patent: Mar. 20, 2001

(54) METHOD FOR ESTERIFICATION OF CARBOXYLIC OR POLYCARBOXYLIC ACID IN THE PRESENCE OF SUPERCRITICAL FLUIDS AND CATALYSTS THEREFOR

(75) Inventors: David Anthony Schiraldi, Charlotte, NC (US); James Seay Brown, Atlanta, GA (US); Karen Chandler, Houston, TX (US); Charles Alan Eckert, Atlanta, GA (US); Jeffrey Scott Hurley, Bartlett, TN (US); David Rene Lamb, Alpharetta, GA (US); Heather Patrick Lesutis; Charles Leonard Liotta, both of Atlanta, GA (US)

(73) Assignee: Arteva North America S.A.R.L., Zurich (CH)

( * ) Notice: Subject to any disclaimer, the term of this patent is extended or adjusted under 35 U.S.C. 154(b) by 0 days.

(21) Appl. No.: 09/187,104

(22) Filed: Nov. 5, 1998

(51) Int. Cl.$^7$ .................................................. C07D 213/72
(52) U.S. Cl. ............................................................ 546/304
(58) Field of Search ............................................. 546/304

(56) References Cited

U.S. PATENT DOCUMENTS

| | | | |
|---|---|---|---|
| 2,937,197 | 5/1960 | Katzschmann | 260/40 |
| 3,052,711 | 9/1962 | Glogan et al. | 524/599 |
| 3,480,587 | 11/1969 | Porter et al. | 260/47 |
| 3,520,853 | 7/1970 | Munakata | 524/599 |
| 4,161,470 | 7/1979 | Calundann | 260/40 |
| 4,431,770 | 2/1984 | East et al. | 524/599 |
| 5,041,194 | * 8/1991 | Mori et al. | 204/58.5 |
| 5,387,619 | 2/1995 | Lee et al. | 521/133 |

OTHER PUBLICATIONS

Haslam, E., *Tetrahedron*, "Recent Developments in Methods for the Esterification and Protection of the Carboxyl Group", 1980, 36. Sheffield, England.

Dillow, A. et al., *Ind. Eng. Chem. Res.* "Kinetics of a Phase–Transfer Catalysis Reacction in Supercritical Fluid Carbon Dioxide", 1966, 35, Atlanta, Georgia.

Chandler, K et al., *Ind. Eng. Chem. Res.*, "Phase–Transfer Catalysis in Supercritical Carbon Dioxide: Kinetic and Mechanistic Investigations of Cyanide Displacement of Benzyl Chloride", 1998, 37, Atlanta, Georgia.

Gurdial, G, et al. *Ind., Eng. Chem. Res.*, "Solubility of o–Hydroxybenzoic Acid in Supercritical Carbon Dioxide", 30, 575, 1991, Kennsington, Australia.

Eckert, C. et al. *Fluid Phase Equilibria*, "Molecular charisma in supercritical fluids", 83, 1993, Amsterdam, Netherlands.

Tsekhanskaya Y., *Russian Journal of Physical Chemistry*, "Diffusion in the System p–Nitrophenol–Water in the Critical Region", 42, 532, 1968.

Brennecke, J. et al, *AIChE Journal,* "Phase Equilibria for Supercritical Fluid Process Design", 35, 9, 1989, Urbana, Illinois.

* cited by examiner

*Primary Examiner*—Zinna Northington Davis
(74) *Attorney, Agent, or Firm*—Gregory N. Clements (57) ABSTRACT

The esterification of a carboxylic or polycarboxylic acid, such as terephthalic acid, with ethylene oxide is conducted in the presence of a supercritical or near critical fluid with an esterification catalyst to form a monoester such as 2-hydroxyethylterephthalate (MHET). The monoester can be easily removed from the involatile terephthalic acid/catalyst bed by continuous extraction with supercritical fluid before subsequent reaction to the diester occurs. The esterification catalyst, such as quaternary ammonium salts, are at least substantially insoluble in the supercritical fluid and capable of withstanding prolonged exposure to elevated temperatures. The process is highly selective to formation of monoesters, and economical. The process can be modified for production of bis-esters or higher esters. The monoesters are polymerizable and can be used as monomers in the production of polyesters such as polyethylene terephthalate.

2 Claims, 3 Drawing Sheets

METHOD FOR ESTERIFICATION OF CARBOXYLIC OR POLYCARBOXYLIC ACID IN THE PRESENCE OF SUPERCRITICAL FLUIDS AND CATALYSTS THEREFOR

FIELD OF THE INVENTION

This invention relates to a method for producing polymerizable mono-hydroxyethyl esters in the presence of a supercritical or near critical fluid and in the presence of a reaction catalyst, or promoter, that is at least substantially insoluble in the supercritical or near critical fluid. The invention also relates to the production of polyesters such as polyethylene terephthalate. The invention is also related to novel quaternary ammonium reaction catalysts that are insoluble in supercritical or near critical fluids and selective to production of monoesters.

BACKGROUND OF THE INVENTION

Commercial production of polyesters such as polyethylene terephthalate (PET), polyethylene naphthalate (PEN) and other polyesters conventionally synthesized from diols and dicarboxylic acids reaches billions of pounds every year. Polyesters are used for manufacturing of a wide variety of products ranging from fabrics to bottles and surgical materials.

Traditional methods for production of polyester require polycondensation of diols with dicarboxylic acids or their lower alkyl esters. These reactions proceed with elimination of low molecular weight by-products such as water or alcohols. Large amounts of low molecular weight compounds produced during polycondensation of polyesters require one or more steps of removal from the polymers. Thus reduction of the amount of water or alcohols during polycondensation of polyesters would significantly simplify the process and reduce the processing cost. Also, reactions involving diacids and diols require an excess of diol to drive the reaction equilibrium forward, thus increasing the reaction cost.

Synthesis of polyester from compounds containing one hydroxy group and one carboxy group such as 4-hydroxybenzoic acid, or 6-hydroxy-2-naphthoic acid disclosed in U.S. Pat. Nos. 4,431,770 and 4,161,470 both issued to Calundann instead of diacids and diols also has an advantage over the diol-diacid process since it does not require excess amounts of diols. However, condensation of these reactants to produce polyesters still produces one molecule of water for each ester link in the polyester.

Synthesis of polyesters from carboxy monohydroxyesters, i.e. monoesters containing both a hydroxy group and a carboxylic acid group, simplifies the synthesis of polyesters. For example, one of the most widely produced polyesters, polyethylene terephthalate (PET) can be produced from the monomer, mono-2-hydroxyethyl terephthalate (MHET), which is typically produced from starting reactant materials of ethylene glycol and terephthalic acid. Recently, the industry has taken a closer look at the reaction mechanisms of producing MHET to determine how to maximize the production of this monomer over other hydroxyethyl terephthalate monomers.

Other starting materials for producing mono-hydroxyesters, are known in the art. U.S. Pat. No. 2,937,297 to Katzschmann et al. discloses production of MHET by re-esterifying an alkali metal salt of the monoesters of terephthalic acid with mono-valent alcohols. The process is complicated and quite costly. Various processes for the esterification of carboxylic acids have been studied in great detail in liquid systems (Haslam, *Tetrahedron,* 1980, 36, 2409–2433). However, esterification of acids in liquid systems is usually expensive due to the high cost of solvents. Also, the reaction usually requires further purification of the monoesters prior to their use as monomers for the synthesis of polyesters.

Recently, it has been reported that supercritical fluids can be used as effective solvents for use in heterogeneous reactions with the reaction product being present in the fluid phase (Dillow, A. et al, *Ind. Eng. Chem. Res.* 1996, 35, 1801–86, Chandler, K., et al, *Ind. Eng. Chem. Res.* 1998, 37, 3252–59). Supercritical fluids (SCF) are very compressible, so they undergo large changes in density, and thus solvation strength, with small changes in temperature or pressure (Gurdial, G., and Foster, N., *Ind. Eng. Chem. Res.* 30, 575, 1991; Eckert, C., and Knutson, B., *Fluid Phase Equil.,* 83, 93, 1993; McHugh, M., and Krukonis, V., *Supercritical Fluid Extraction: Principles and Practice,* Butterworth-Heinemann, Stoneham Mass., 1994). The addition of cosolvents can also greatly affect the solvating power of a SCF. They have high diffusivities and low viscosities, making them ideal candidates for use as solvents in heterogeneous reactions (See Tsekhanskaya, Y., Russ. *J. Phys. Chem.,* 42, 532, 1968; Brennecke, J., *AIChE Journal,* 35, 9, 1989). Unlike a liquid solvent, a SCF can be easily and completely separated from the reaction products by depressurization. This is advantageous over processes utilizing organic solvents which require a costly step of solvent removal. Also, the solvents often cannot be removed completely, thus contaminating the resulting product. It is especially important to completely remove solvent when the reaction product is used as a reactant, for example, as a monomer in a polymerization reaction. Solvent residue will contaminate resulting polymers and often act as a plasticizer, limiting the utility of the polymer.

Using supercritical fluids as a solvent to produce polyster is well known and are described in U.S. Pat. No. 5,387,619 to Lee et al.; U.S. Pat. No. 3,480,587 to Porter et al.; and U.S. Pat. No. 3,052,711 to Glogan et al. Producing hydroxyethylester monomers from ethylene oxide and terephthalic acid is known from U.S. Pat. No. 3,520,853 to Munakata.

The present invention provides a process for synthesis of monoesters, such as mono-hydroxyethyl terephthalate, using a reaction catalyst or promoter, such as quaternary ammonium catalysts, to reduce the production of a condensation by-product, such as water. The process is conducted in the presence of a supercritical or near critical fluid, and, thus, does not require costly steps of separation of the products from the reaction media. Separated and recovered monoesters can be directly used as monomers in the synthesis of polyesters. Production of polyesters from monohydroxyesters, enables production of polyesters with the amount of water produced during polycondensation being half that produced in a conventional diol/diacid process. Therefore, less heat is required to remove the water, and processing costs are significantly reduced. In addition, a one-to-one ratio of reacting groups on the monomer simplifies the polymerization reaction.

SUMMARY OF THE INVENTION

An esterification of polycarboxylic acids with ethylene oxide or substituted ethylene oxide where the resulting polymerizable ester product is extracted or removed from the solid reactants and catalysts may be achieved in the presence of an esterification catalyst and in the presence of a supercritical or near critical fluid (SCF). The ester extracted by the SCF can then be easily forwarded to another reactor and polycondensed to produce conventional polyesters. For optimum kinetics and phase behavior, the catalyst, or promoter, for the esterification reaction is a catalyst that is able to withstand high temperatures of up to 150° C. for a prolonged time. The catalysts should also be at least substantially insoluble in the mixture of the supercritical or near critical fluid and ethylene oxide component at the reaction conditions. The present invention also provides novel esterification catalysts, such as quaternary ammonium salts, which are highly selective to the production of monoesters from polycarboxylic acids. The esterification process according to the invention eliminates the production of condensation by-products such as water.

In the broadest sense, the present invention contemplates the product of esters by reacting carboxylic or polycarboxylic acids with ethylene oxide or substituted ethylene oxide in a supercritical or near supercritical fluid with a catalyst which is at least substantially insoluble in supercritical or near supercritical fluid. When monocarboxylic acids are employed, an ester product results which cannot be polymerized. Nevertheless, these esters have many uses such as in flavorings, solvents, or lubricants. Polycarboxylic acids, such as dicarboxylic acids can be polymerized to form polyesters.

DETAILED DESCRIPTION OF THE INVENTION

A process for esterification of polycarboxylic acids according to the present invention allows for efficient production of esters that can be used as monomers for polyester production. The process is economical and very effective in production of monoesters from polycarboxylic acids without production of a significant amount of side products such as bi- or tri-ester. Monoesters are obtained by esterification of an organic acid with ethylene oxide or a substituted ethylene oxide such as any compound represented by the Formula (I) (Compound I) in the presence of an esterification catalyst or promoter and in the presence of a supercritical or near critical fluid (SCF):

(I)

wherein $R_1$–$R_4$ are the same or different and are selected from hydrogen, C1–C4 alkyl or halogenated alkyls. Ethylene oxide, propylene oxide and epichlorohydrin are preferred compounds for use in the present invention.

As used herein, reference to supercritical fluids as solvents for a compound, such as the compound of Formula I or the reaction product of the present invention, connotes the dissolving of the compound by the supercritical fluid or vice versa. However, the invention also includes the dispersion and suspension of the compound by the supercritical fluid. Thus, it is to be understood that solvency, and carrier are intended to mean that the additive is rendered into a more dilute flowable condition by virtue of the supercritical fluid or high pressure gas. It includes dissolving, suspending, entraining, and/or dispersing of the compound by the supercritical fluid or high pressure gas or vice versa so that the admixture is characterizable by a lower viscosity and a more fluid composition for the transport of the compound.

Near critical fluids also demonstrate solubility characteristics and other pertinent properties similar to those of supercritical fluids. The solute may be a liquid at the supercritical temperature, even though it is a solid at lower temperatures. In addition, fluid modifiers or cosolvents can often alter supercritical fluid properties significantly, even in relatively low concentrations, greatly increasing solubility for some solutes.

As used herein, the phrase "SCF" indicates a compound above, at, or slightly below the critical temperature and pressure of that compound. A supercritical fluid is a substance which has been subjected to conditions of pressure and temperature that equal or exceed both of those thermodynamic conditions at the critical point for that substance.

At pressures above the critical point, the resulting supercritical fluid, or "dense gas" will obtain densities approaching those of a liquid and will assume some of the properties of a liquid. These properties are dependent upon the fluid composition, temperature, and pressure. Just above the critical temperature, small changes and pressure result in large changes in the density of the supercritical fluid. The "liquid-like" behavior of a supercritical fluid at higher pressures results in greatly enhanced solubilizing capabilities compared to those of the "subcritical" compound with higher diffusion coefficients and an extended useful temperature range compared to liquids.

A fluid near, but below, its critical point, i.e. a near critical fluid, or at or above its critical point, i.e. a supercritical fluid has liquid-like densities and excellent mass transport properties. This results in excellent abilities in tuning and enhancement of solubilities. Small changes in pressure create large changes in the density of the fluid. This results in large changes in the solubility of a compound or series of compounds. In the region near the critical point, the system can be fine tuned to selectively solubilize a compound from a mixture. The differences in solubility of the various compounds involved in the reaction are taken advantage of in the design of the reaction process. The monoesters produced in this process are selectively extracted, separated, removed, or carried from the reaction media by the supercritical fluid or near critical fluid while the unreacted acid and the catalyst remain in the reaction zone and are not extracted or otherwise removed by the SCF.

The esterification reaction for production of monoesters can be generally exemplified by the following equation using ethylene oxide as Compound I and terephthalic acid as a starting organic acid:

In case where the starting acid contains more than one carboxylic acid group, the process can be modified to produce either a monoester by esterifying only one of the carboxylic acid groups. In other embodiments, a bi-, tri- or higher ester may be produced by esterifying as many of the available carboxylic groups as desired by the end user, wherein the reaction continues after the esterification of the first carboxylic group to esterify additional carboxylic groups.

The extent of esterification, however, can be easily controlled and limited to production of monoesters (ME), most suitable for synthesis of conventional polyesters, according to the process according to the present invention.

Figure 1:
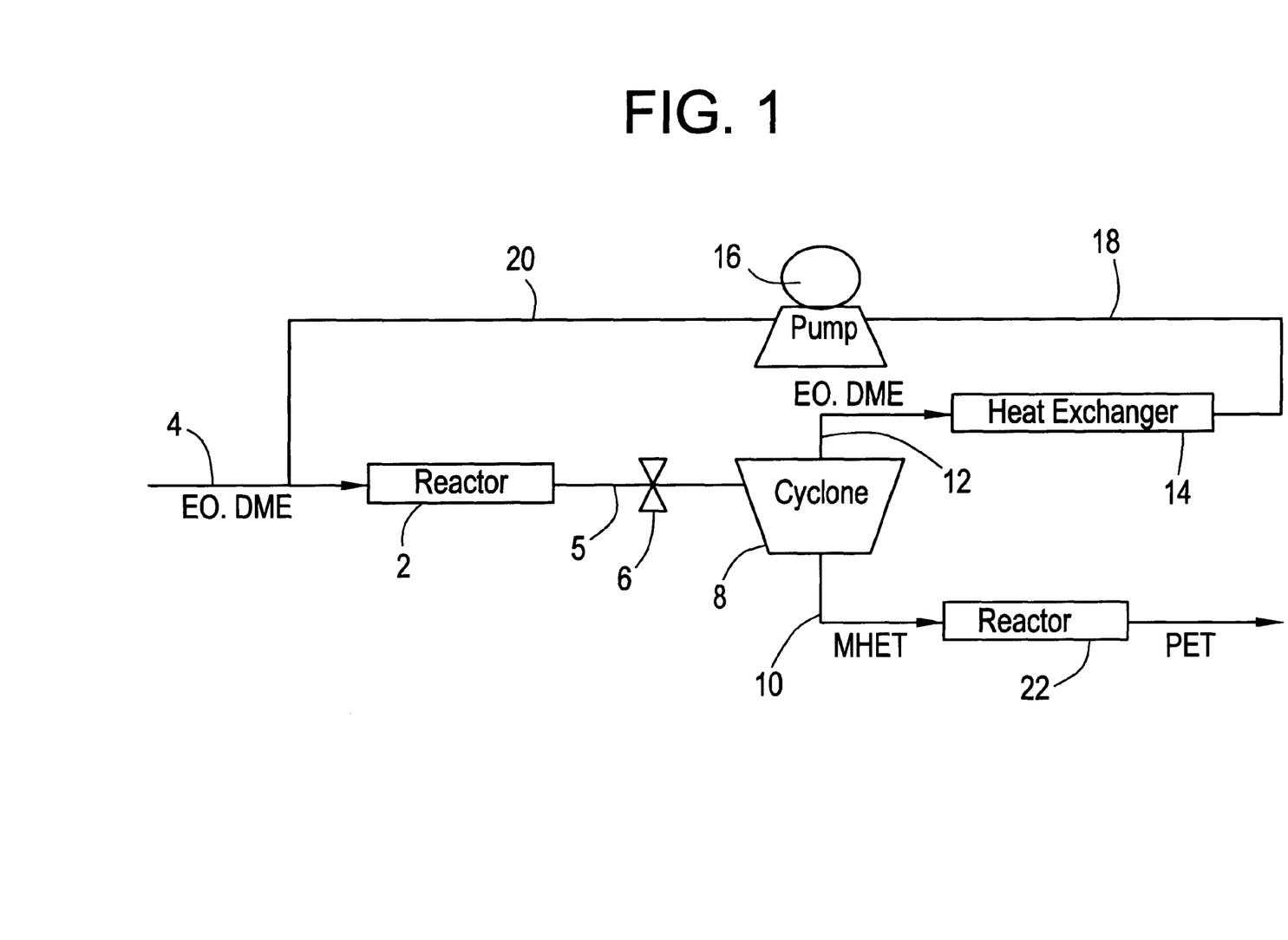
FIG. 1 shows a diagram of a process for producing monohydroxyesters according to the invention.

Schematic representation of the process according to one aspect of the present invention is illustrated by the diagram shown in FIG. 1. As shown in FIG. 1, the process may be conducted in a packed bed reactor 2 by flowing, under elevated pressure, a mixture 4 of SCF carrier (such as dimethyl ether, DME) and Compound I (such as ethylene oxide, EO) over a packed bed comprising an acid and an esterification catalyst. Compound I reacts with the acid thus producing a monoester which is then carried out of the reaction site by effluents 5 before it can further react to produce bis- or higher-esters depending on the functionality of the starting acid. The effluents 5 may then be depressurized by passage through a pressure reduction valve 6 and forwarded to a separating device, such as a cyclone 8 where solid ester is separated or removed via line 10 from gaseous components (e.g. EO and DME) which exit via line 12. The gaseous components comprising unreacted ethylene oxide and SCF then enter a heat exchanger 14. After the gaseous mixture of the EO and SCF is cooled and liquidified in the heat exchanger 14, it is then preferably recycled back to the reactor 2 by pump 16 via lines 18 and 20. If the recovered monoester is capable of being polymerized, then it may be forwarded to a second reactor 22 for polycondensation using methods known in the art, to form a polyester such as polyethylene terephthalate or other polyesters, depending on the starting acid.

The carboxylic or polycarboxylic acids which may be employed for esterification according to the process of the invention are any acids that are solid at the reaction temperature. Preferably, the acid had a melting point greater than about 100°. Also, low solubility of the acid in the supercritical or near critical fluid at the reaction conditions assures that the unreacted acid remains in the reaction zone and is not carried outside of the reactor with the flow of the supercritical or near critical fluid. The acids can be monofunctional, i.e. a monoacid, bifunctional, i.e. a diacid, a polyfunctional acid containing more than two carboxylic groups, or mixtures thereof. The organic acid can be an aliphatic, cycloaliphatic or aromatic acid. Examples of organic acids which may be used are succinic, caprylic, capric, lauric, myristic, sebacic, stearic, benzoic, terephthalic, isophthalic, naphthalene dicarboxylic acid, anthracene dicarboxylic acids, and anthraquinone dicarboxylic acid or mixtures of 2 or more of these. Preferred acids are difunctional carboxylic acids among which aromatic acids such as terephthalic, isophthalic, naphthalene dicarboxylic acids and anthracene dicarboxylic acids, and mixtures thereof are most preferred.

Exemplary compounds which are known to have utility as supercritical fluids are given in Table 1:

TABLE 1

Examples Of Supercritical Solvents

| Compound | Boiling Point (° C.) | Critical Temperature (° C.) | Critical Pressure (atm) | Critical Density (g/cm$^3$) |
|---|---|---|---|---|
| Dimethylether | −24.9 | 127 | 53.7 | 0.242 |
| CO$_2$ | −78.5 | 31.3 | 72.9 | 0.448 |
| NH$_3$ | −33.35 | 132.4 | 112.5 | 0.235 |
| H$_2$O | 100.00 | 374.15 | 218.3 | 0.315 |
| N$_2$O | −88.56 | 36.5 | 71.7 | 0.45 |
| Methane | −164.00 | −82.1 | 45.8 | 0.2 |
| Ethane | −88.63 | 32.28 | 48.1 | 0.203 |
| Ethylene | −103.7 | 9.21 | 49.7 | 0.218 |
| Propane | −42.1 | 96.67 | 41.9 | 0.217 |
| Pentane | 36.1 | 196.6 | 33.3 | 0.232 |
| Methanol | 64.7 | 240.5 | 78.9 | 0.272 |
| Ethanol | 78.5 | 243.0 | 63.0 | 0.276 |
| Isopropanol | 82.5 | 235.3 | 47.0 | 0.273 |
| Isobutanol | 108.0 | 275.0 | 42.4 | 0.272 |
| Cyclohexanol | 155.65 | 356.0 | 38.0 | 0.273 |
| Xenon | −108.2 | 16.6 | 57.6 | 0.118 |
| Krypton | −153.2 | −63.8 | 54.3 | 0.091 |
| Nitrogen | −195.8 | −147.1 | 33.5 | 0.311 |

Supercritical or near critical fluids (SCF) suitable for the process of the invention are very compressible fluids so they undergo large changes in density, and thus solvation strength, with small changes in temperature or pressure. Also, a mixture of a SCF with at least one cosolvent can be used in the invention. Addition of cosolvents can greatly affect the solvating power of SCF. In embodiments of the invention, the supercritical or near critical fluid that is employed as a solvent may be chosen so that neither the organic acid nor the esterification catalyst are significantly soluble in a mixture of ethylene oxide, or substituted ethylene oxide, and the SCF. If either component is too soluble, it will be carried out of the packed bed reactor by the flowing solvent. Second, the reaction product, i.e. the monoester, or, if desired a higher ester, should be soluble in a mixture of ethylene oxide (or substituted ethylene oxide) and the SCF, so that it can be removed from the reaction site before it reacts further to form higher esters, such as a bis ester, in the case where a monoester is the desired product.

Generally, the solubility of the reaction product in the supercritical or near critical fluid carrier should be at least 10 times higher than the solubility of either the acid or the esterification catalyst. A different SCF may be required for different starting compounds and different resulting products. Solubilizing properties of the SCF and/or mixtures of SCF with co-solvents may be evaluated or measured for any solid substance of interest, such as acids and catalysts using an apparatus as shown in FIG. 2.

Figure 2:
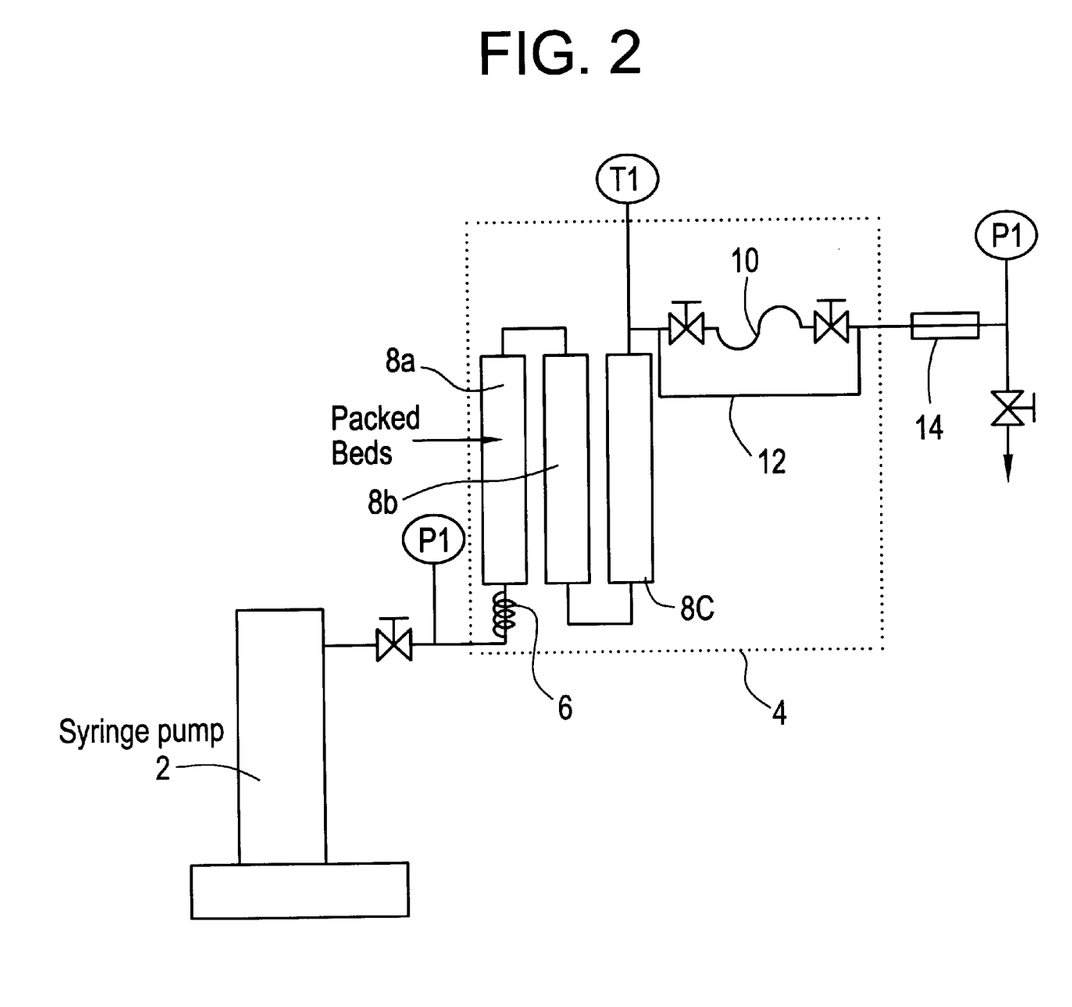
FIG. 2 shows an apparatus for determination of the solubility properties of supercritical fluids for use in the present invention.

As shown in FIG. 2, first, the pure solvent or solvent/cosolvent mixture is loaded into an ISCO 260D syringe pump 2. This fluid is then pumped into an HP5890 Series II gas chromatograph oven 4 which is used only as a thermostated oven. The fluid passes through a tubing coil 6 to allow the fluid temperature to equilibrate. The fluid then passes through three tubes 8a, 8b, and 8c packed with the solid of interest; three tubes are used to ensure saturation of the fluid. The saturated fluid then passes through either a sample loop 10 or a bypass loop 12. It then flows through a carbon packed bed 14 to trap the solid and finally flows out of the system into a vented hood. Once the system is at a specified pressure, the saturated fluid flows through the system, via the bypass loop 12, for one residence time. The bypass loop 12 is used to prevent any accumulation of the solid on the walls of the sample loop 10 due to temperature or pressure fluctuations. The bypass loop 12 is then closed, and the sample loop 10 is opened. Once the sample loop 10 is filled with saturated fluid, it is removed, depressurized and analyzed on an HP8453 UV-VIS spectrophotometer. The intensity of the solid absorbance at $\lambda_{max}$ yields the amount of solid in the sample loop 10 of known volume, and the mole percent of solid in a saturated solution is then calculated using the solvent/cosolvent density using the Peng-Robinson equation of state.

Preferred SCF(s) for the esterification of aromatic acids are dimethylether (DME) or mixtures of DME with up to 50 mole % of carbon dioxide cosolvent or with up to 10 weight % of ethylene glycol dimethylether cosolvent, based on the total amount of the mixture. Another example of a cosolvent which may be employed is acetonitrile. Acetonitrile cosolvent may be used alone or in combination with other cosolvents such as ethylene glycol dimethylether and carbon dioxide.

The esterification catalyst, or promoter, can be selected and designed through a structure activity relationship, and several novel quaternary ammonium esterification catalysts were designed and synthesized. It should also be nonvolatile, to ensure that it does not contaminate the volatile products. To minimize the amount of catalyst removed from the reaction zone by the supercritical fluid it is essential that the esterification catalysts are insoluble, or substantially insoluble in the SCF at the reaction conditions. In addition, it should be solid at the reaction temperatures, thermally stable and produce an economically viable reaction rate. Preferably, the esterification catalysts have a melting point above about 100° C. Also, if a monoester product is the product of choice, a successful esterification catalyst, in combination with reaction fluid and reaction conditions, should aid in selective production of the monoester over the diethoxylated product.

Quaternary ammonium salts and substituted amines such as those disclosed in U.S. Pat. No. 3,520,853, while suitable as catalysts or promoters for an esterification reaction, can easily degrade. In the presence of a strong base, beta-hydrogen elimination can occur leaving the tertiary amine and an alkene. Also, at elevated temperatures the quaternary ammonium salt can thermally degrade through a nucleophilic displacement. However, both of these degradation mechanisms can be avoided through designing the quaternary ammonium salt to have either a hindered or no beta hydrogen.

Figure 3:
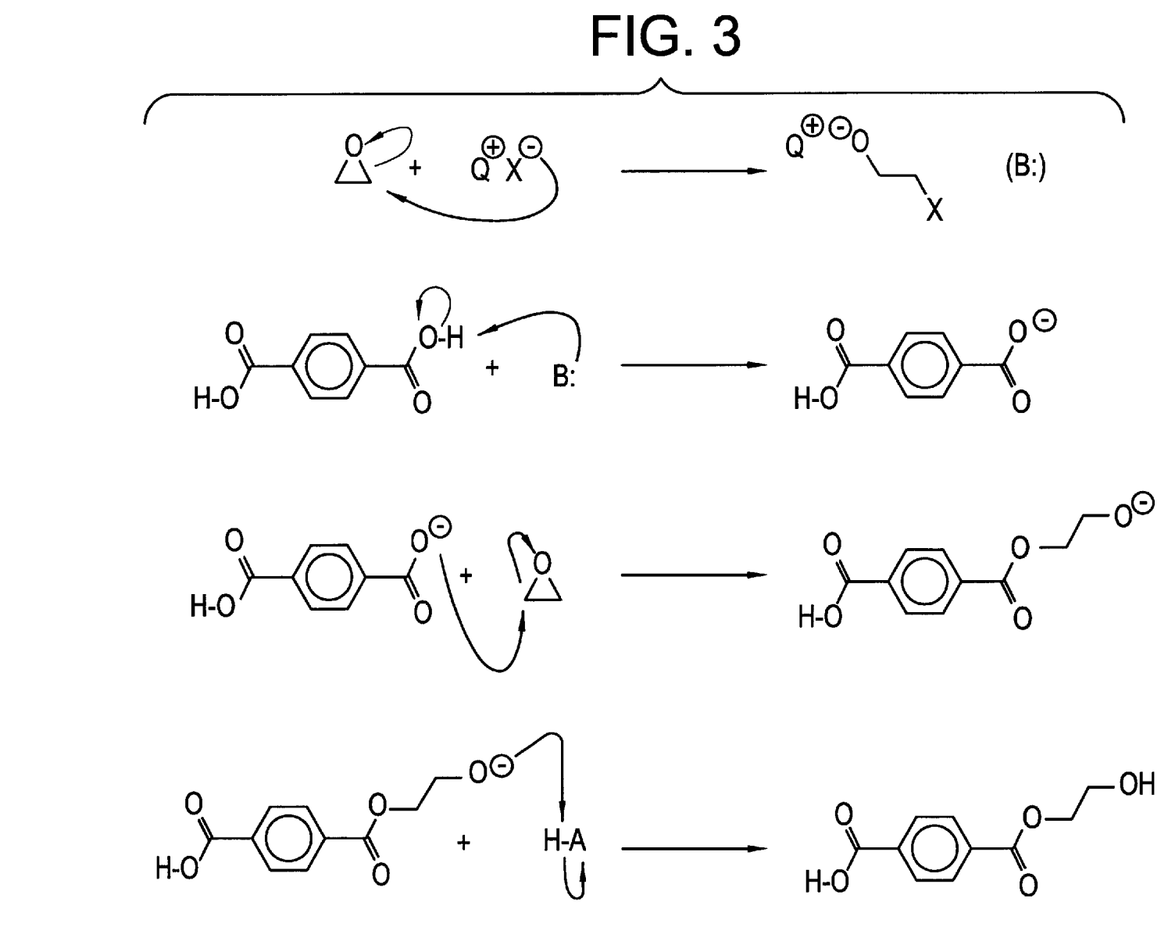
FIG. 3 shows a proposed mechanism for the esterification reaction of the present invention.

Another consideration in choosing or designing a suitable catalyst, or promoter, is that it is desirable to have a quaternary salt in which the ion pairs are loosely associated. The loose association should result in higher rates of reaction according to the proposed esterification mechanism. In the proposed mechanism illustrated in FIG. 3, the anion of the quaternary salt would perform a nucleophilic attack on ethylene oxide. This step of the mechanism would be much more likely if the anions were loosely associated with the quaternary ammonium cation. H-A in FIG. 3 is any proton donor compound, such as terephthalic acid.

The "tightness" of the ion pair between the quaternary ammonium cation and the anion can be controlled through the design of the structure. For instance, when designing a pyridine-based quaternary ammonium compound, electron donating groups on the pyridine ring will help to delocalize the positive charge on the quaternized nitrogen in effect making it "less positive". In the same way, when the pyridine structure is quaternized with a benzyl compound, electron donating groups on the benzene ring will also donate electron density to the positive charge making the ion pair more loosely associated. The substituent effect of functional groups on the benzene ring, however is not as strong as that of the functional groups on the pyridine ring. Substituents on the pyridine ring have a direct resonance effect, while substituents on the benzene ring are insulated by the methylene group and therefore only have an inductive effect on the tightness of the ion pair.

Catalysts of the present invention for promoting the esterification reaction in accordance with the invention are exemplified by the catalysts of formulas (II) and (III). The catalysts of formula II are:

(II)

wherein $R_1$ and $R_2$ are, independently, hydrogen, $C_1$–$C_{10}$ linear or branched alkyl groups, X represents an anion and $R_3$ is hydrogen, a straight chain or branched $C_4$–$C_{10}$ alkyl, or a group represented by the following formula:

wherein Z is selected from hydrogen, halogens, nitro, alkoxy and groups represented by the formula:

wherein $R_1$, $R_2$ and X are as defined above.

Catalysts of formula II may be produced by reacting an N,N-disubstituted amino pyridine compound with a compound corresponding to $R_3$ and bearing a leaving group (such as halide, tosylate, mesylate or the like) such that nucleophilic displacement of the leaving group occurs, giving rise to an N,N-disubstituted pyridinium salt. Exemplary reaction temperatures may range from about 70° C. to about 150° C. at about atmospheric pressure or under reflux.

The catalysts of formula III are:

(III)

wherein $R_1$–$R_4$ are the same or different and are selected from straight chain or branched $C_3$–$C_{10}$ alkyls.

Catalysts of formula III may be obtained by reacting two moles of a tetraalkyl ammonium hydroxide of the formula $R_1R_2R_3R_4N^+OH^-$ with a dicarboxylic acid (DA) to form a salt of the formula $[R_1R_2R_3R_4N^+]_2DA^{-2}$. Exemplary reaction temperatures may range from about 70° C. to about 150° C. at about atmospheric pressure or under reflux.

The catalysts of formula IV may also be used to produce monohydroxyesters in accordance with the present invention:

(IV)

wherein X is an anion.

The dichloride salt of formula IV (i.e. benzyl viologen dichloride) is commercially available from Aldrich Chemical Company. Replacement of the counterion can be accomplished by conventional ion exchange.

The reaction rate is related to the tightness of the ion pair in the esterification catalyst, or promoter. The reaction scheme proposed for the mechanism of esterification in this system indicates that the anion of the esterification catalysts, such as quaternary ammonium salts, plays an important role. The anion performs a nucleophilic attack on the ethylene oxide component to open the ring and form an oxygen anion. This nucleophilic attack is more likely if the structure of the catalyst is such that the anion and cation are more loosely associated. In a polar aprotic liquid solvent the order of nucleophilicity is Cl—>Br—>I—. In supercritical DME (which is also a polar aprotic solvent), it seems that the order is reversed. Bromide catalysts are consistently more reactive than chloride catalysts. Examples of anions (X) which may be used in the catalysts of the present invention are chloride, bromide, iodide, hydroxide, methoxide, ethoxide, other lower alkoxides, aryloxides, cyanide, thiocyanide, acetate, nitrate or any other counterion with a nucleophilicty of greater than 1 as calculated from the Swain-Scott equation. Preferred anions are chloride, bromide, iodide and thiocyanate.

Preferred catalysts are N-2-ethyl-hexyl(4-dimethyl amino) pyridinium chloride (EHPC), N-2-ethyl-hexyl(4-dimethyl amino) pyridinium bromide (EHPB), N-2-ethyl-hexyl(4-dimethyl amino) pyridinium iodide (EHPI), N-2-ethyl-hexyl(4-dimethyl amino) pyridinium thiocyanide (EHPT), N-neopentyl (4-diethyl amino) pyridinium chloride (NPC), N-benzyl-(N,N-dimethylamino)pyridinium chloride (BPC), N-p-chlorobenzyl-(N,N-dimethylamino)pyridinium chloride (CBPC), N-p-nitrobenzyl(N,N-dimethylamino) pyridinium chloride (NBPC), N-p-nitrobenzyl(N,N-dimethyl-amino)pyridinium bromide (NBPB), N-p-methoxybenzyl(N,N-dimethyl-amino)pyridinium chloride (MBPC), Xylyl-bis N,N,-(N,N,-dimethylaminopyridinium) dichloride (XPDC), benzyl viologen dichloride (BVDC), bis-(tetrabutylammonium) terephthalate (TBTA), and mixtures thereof.

The catalysts, or promoters, are employed in catalytically effective amounts. Exemplary amounts of the catalyst may be from about 0.1 mole % to about 15 mole %, preferably from about 1 mole % to about 10 mole % of the organic acid. If the amount of catalyst is lower than 0.1 mole %, the reaction rate becomes too slow, and if the amount of catalyst is above 15 mole %, while the reaction rate increases, the process becomes too expensive.

The esterification reaction is conducted at temperatures below the melting temperature of both the organic acid and the esterification catalyst. Exemplary reaction temperatures range from about 25° C. to about 250° C., preferably from about 75° C. to about 150° C. If the temperature is below 25° C., the reaction rate is very slow. Reaction temperatures above 250° C. may not be practical because both the catalyst and the acid should remain at least substantially solid at the reaction temperatures. However, if the melting point of both the catalyst and the acid is above 250° C., and both the acid and the catalyst are substantially insoluble in the SCF at the reaction conditions, it is advantageous to use temperatures above 250° C. to increase the conversion rate.

The reaction pressure employed depends upon the temperature of the reaction and the SCF so that the solubility properties of the SCF are such that the monohydroxy ester product is at least substantially dissolved or separated from the esterification catalyst and the organic acid. Exemplary reaction pressures range from about 500 psig to about 5000 psig depending on the critical pressure of the compressed solvent (SCF).

The present invention is further illustrated in the following examples where all parts, percentages, and ratios are by weight, all temperatures are in ° C., and all pressures are atmospheric unless otherwise indicated:

EXAMPLES 1–12

Esterification Catalyst Synthesis

In Examples 1–12 twelve esterification catalysts were synthesized and the resulting products were subjected to NMR, IR and CHN elemental analyses. The structures and abbreviations for the twelve catalysts are:

Example 1
N-2-ethyl-hexyl(4-dimethyl amino) pyridinium chloride (EHPC)

A mixture of 4.0952 g (mol)2-ethyl-hexyl mesylate, 1.8682 g 4-diethylamnino pyridine, and 25 mL dry toluene was flushed with argon, brought to reflux and allowed to stir for 3 hours. The solution was allowed to cool to room temperature, and the solvent was removed via rotary evaporation. The resulting residue was dissolved in 50 mL methylene chloride, and washed with saturated sodium chloride 3×(50 mL )@3 minutes each. The aqueous layers were combined and extracted with 50 mL methylene chloride. The organic layers were combined and dried over magnesium sulfate. The solvent was again removed with rotary evaporation, and resulting residue was recrystallized from methylene chloride/diethyl ether, to give 3.54 g white crystals (88%) with a melting point of 191–192° C. Calculated for $C_{15}H_{27}N_2Cl$: C, 66.5197%; h, 10.0476%; N, 10.3430%. Found: C, 61.29%; H, 9.59%; N, 9.57%. 1H NMR ($CDCl_3$ 300 MHZ): δ 0.85 (m 6H), 6 1.21 (m 8H), δ 1.80 (m 1H), δ 3.25 (s 6H), δ 4.12 (d 2H), δ 7.10 (d 2H aromatic), 6 8.38 (d 2H aromatic).

Example 2
N-2-ethyl-hexyl(4-dimethyl amino) pyridinium bromide (EHPB)

The same procedure was used as for the chloride analog of Example 1, except the crude product was washed with saturated sodium bromide, as opposed to sodium chloride and gave 83% yield. Calculated for $C_{15}H_{27}N_2Br$: C, 57.1416%; H, 8.6310%; N, 8.8848%. Found: C, 56.99%; H, 8.65%; N, 8.75%. 1 H NMR ($CDCl_3$ 300 MHZ): δ 0.88 (m 6H), δ 1.28 (m 8H), δ 1.85 (m 1H), δ 4.19 (d 2H), δ 7.10 (d 2H aromatic), δ 8.39 (d 2H aromatic).

Example 3
N-2-ethyl-hexyl(4-dimethyl amino) pyridinium iodide (EHPI)

The same procedure was used as for the chloride analog of Example 1, except the crude product was washed with saturated sodium iodide, as opposed to chloride and gave yellow crystals, 71%. 1 H NMR ($CDCl_3$ 300 MHZ): δ 0.88 (m 6H), δ 1.28 (m 8H), δ 1.85 (m 1H), δ 4.15 (d 2H), δ 7.08 (d 2H aromatic), δ 8.30 (d 2H aromatic).

Example 4
N-2-ethyl-hexyl(4-dimethyl amino) pyridinium thiocyanide (EHPT)

The same procedure was used as for the chloride analog of Example 1, except the crude product was washed with saturated sodium thiocyanide, as opposed to chloride and gave a viscous orange oil, 96%. 1 H NMR ($CDCl_3$ 300 MHZ): δ 0.88 (m 6H), δ 1.28 (m 8H), δ 1.85 (m 1H), δ 4.15 (d 2H), δ 7.08 (d 2H aromatic), δ 8.20 (d 2H aromatic).

Example 5
N-neopentyl (4-diethyl amino) pyridinium chloride (NPC)

A mixture of 3.4584 g neopentyl mesylate and 2.1180 g dimethylamino pyridine was stirred and heated to 130° C. for 68 hrs. The reaction was allowed to cool, resulting in a brown solid. The solid was dissolved in minimum amount of water and basified with NaOH. The solution was then acidified with concentrated HCl to a pH below 2. NaOH was then added to a pH of approximately 8. The aqueous layer was then extracted with methylene chloride 3×@25 mL each, and the organic layers were combined and dried over magnesium sulfate. The solvent was removed and the solid was dissolved in a minimum amount of hot chloroform. Diethyl ether was then added to the fog point. The solution was then cooled and the pure product crystallized as plates to give 1.72 g (43%). Calculated for $C_{12}H_{21}N_2Cl$: C, 63.0046%; H, 9.2523%; N, 12.2455%. Found: C, 62.90; H, 9.19%; N, 12.32%. 1H NMR (CDCl$_3$ 300 MHZ): δ 1.02 (s 9H), δ 3.30 (s 6H), δ 4.20 (s 2H), δ 7.02 (d 2H aromatic), δ 8.41 (d 2H aromatic).

Example 6
N-benzyl-(N,N-dimethylamino)pyridiiiium chloride (BPC)

A mixture of 4.9227 g (0.0402 mol) N,N dimethylaminopyridine, 4.63 mL (0.0402 mol) benzylchloride, and approximately 10 mL toluene, were added to a clean, dry 25 mL round bottom flask fitted with a stir bar, condensor and drying tube. The reaction flask was then lowered into an oil bath at 80° C., and stirred. The solution was completely miscible initially, then after five minutes became a white solid. The reaction was allowed to react over night, and was then cooled to room temperature. The toluene was removed via rotary evaporation, and the resulting solid was recrystallized in ethanol/ether to give 7.9804 g (79.8%). Calculated for $C_{14}H_{17}N_2Cl$: C, 67.5983%; H, 6.8880%; N, 11.2615%. Found: C, 66.34%; H, 7.01%; N, 11.06%. 1H NMR (D$_2$O 300 MHZ): δ 2.95 (s 6H), δ 5.10 (s 2H), δ 6.62 (d 2H), δ 7.22 (m 5H), δ 7.85 (d 2H). Melting point 257–258° C.

Example 7
N-p-chlorobenzyl-(N,N-dimethylamino)pyridinium chloride (CBPC)

A mixture of 1.1313 g (0.00706 mol) p-chlorobenzylchloride, 0.8623 g (0.00706 mol) dimethylaminopyridine, and approximately 10 mL toluene were added to a clean, dry 50 mL round bottom flask equipped with a stir bar, condensor, and drying tube. The reaction apparatus was then lowered into an oil bath at 110° C. The solution became miscible immediately and after 5 minutes a thick white precipitate formed. The reaction was allowed to continue overnight, and after 12 hours was cooled to room temperature. The solvent was removed via rotary evaporation. The resulting solid was recrystallized from ethanol/diethylether to give 1.790 g (89.5%). Calculated for $C_{14}H_{16}N_2Cl_2$: C, 59.3765%; H, 5.6944%; N, 9.8917%. Found: C, 57.63%; H, 5.88%; N, 9.59%. 1H NMR (D$_2$O 300 MHZ): δ 3.02 (s 6H), δ 5.15 (s 2H), δ 6.71 (d 2H), δ 7.18 (d 2H), δ 7.30 (d 2H), δ 7.90 (d 2H). Melting point 208–210° C.

Example 8
N-p-nitrobenzyl(N,N-dimethylamino)pyridinium chloride (NBPC)

To a 50 mL round bottom flask equipped with a stir bar, condensor, and drying tube, was added 2.923 g (0.017 mol) p-nitrobenzylchloride, 2.078 g (0.017 mol) N,N-dimethyaminopyridine, and approximately 10 mL toluene. The reaction flask was lowered into an oil bath at 80° C., and stirred. After about 10 minutes, a white precipitate formed. After four hours, the reaction flask was cooled to room temperature, and the solvent was removed via rotary evaporation. The resulting solid was recrystallized from methanol/isopropanol to give 4.055 g (81.1%) of pale yellow crystals 1H NMR (CDCl$_3$ 300 MHZ): δ 3.20 (s 6H), δ 6.05 (s 2H), δ 6.88 (d 2H), δ 7.92 (d 2H), δ 8.15 (d 2H), δ 9.02 (d 2H). Melting point 239° C. (decomposition).

Example 9
N-p-nitrobenzyl(N,N-dimethylamino)pyridinium bromide (NBPB)

To a clean dry 100 mL round bottom flask fitted with a stir bar, condenser and drying tube, was added 1.4065 g (0.006505 mol) p-nitrobenzylbromide, 0.7233 g (0.005913 mol) N,N-dimethylaminopyridine, and 40 mL toluene. Heated to 93° C. and stirred overnight (avoided refluxing due to violent degradation of p-nitrobenzylbromide). Toluene was removed via rotary evaporation, and the resulting solid was recrystallized from ethanol/ether to give 1.79 g (89.5%) of pale yellow crystals. Calculated for $C_{14}H_{16}N_3O_2Br$: C, 49.720%; H, 4.768%; N, 12.425%. Found: C, 49.67%; H, 4.75%; N, 12.37%. 1H NMR (D$_2$O 300 MHZ): δ 3.25(s 6H), δ 6.02 (s 2H), δ 6.76 (d 2H), δ 7.80 (d 2H), δ 8.22 (d 2H), δ 8.80 (d 2H). Melting point 283° C. (decomposition).

Example 10
N-p-methoxybenzyl(N,N-dimethylamino)pyridinium chloride (MBPC)

To a clean dry 50 mL round bottom flask equipped with a stir bar, condenser, and drying tube, was added 0.8768 g (0.007174 mol) N,N-dimethylaminopyridine, and 0.97 mL (0.007174 mol) p-methoxybenzylchloride. The reaction flask was then lowered into an oil bath at 100° C. and stirred for 30 minutes. A white precipitate formed after 5 minutes. The crude solid was recrystallized from ethanol/ether to give 1.7181 g (86%) of white crystals. Calculated for $C_{15}H_{19}N_2OCl$: C, 64.2557%; H, 6.8299%; N, 9.9910%. Found: C, 61.75; H, 6.97%; N, 9.59%. 1H NM (CDCl$_3$ 300 MHZ): δ 3.21(s 6H), δ 3.78 (s 3H), δ 5.57 (s 2H), δ 6.90(m 4H), δ 7.50(d 2H), δ 8.71 (d 2H). Melting point 166–167° C.

Example 11
Xylyl-bis N,N,-(N,N,-dimethylaminopyridinium) dichloride (XPDC)

To a clean, dry 25 mL round bottom flask fitted with a stir bar, condenser, and drying tube, was added 1.7265 g (0.01413 mol) N,N,-dimethylaminopyridine, 1.1776 g (0.006728 mol) dichloroxylene, and about 10 mL toluene. The reaction flask was then lowered into an oil bath at about 100° C. and stirred overnight. The reaction was then cooled and the solvent was removed via rotary evaporation. The resulting solid was then recrystallized from ethanol/ether to give white crystals, 1.80 g (64%). Calculated for $C_{22}H_{28}N_4Cl_2$: C, 63.0054%; H, 6.7290%; N, 13.3589%. Found: C, 61.69; H, 6.79%; N, 13.03%. 1H NMR (D$_2$O 300 MHZ): δ 3.00(s 6H), δ 5.16 (s 2H), δ 6.66 (d 4H), δ 7.22 (m 4H), δ 8.85 (d 4H). Melting point 310° C. (decomposition).

Example 12
Bis-(tetrabutylammonium) terephthalate (TBTA)

To a clean, dry 500 mL round bottom flask equipped with a stir bar, Dean-Starke adapter, condenser, drying tube, and nitrogen inlet, was added 10.0 mL (0.015411 mol) of a 40 wt % aqueous solution of tetrabutylammonium hydroxide, 1.2801 (0.007705 mol) terephthalic acid, 100 mL ethanol, and 150 mL benzene. Lowered apparatus into an oil bath and heated to reflux for 6 hours. The azeotrope distilled at 64.9° C. and the reaction was allowed to remove water overnight. The reaction was cooled to room temperature, and the solvent was removed via rotary evaporation. A sample of the crude product was shown to be very soluble in water, and an NMR was taken which showed the absence of terephthalic acid. The wax-like solid was recrystallized from ethanol/ether to give white crystals, 3.9104 g (78%). Calculated for $C_{40}H_{76}N_2O_4$: C, 740219%; H, 11.8019%; N, 4.3161%. Found: C, 69.16; H, 11.74%; N, 4.02%. 1H NMR (CDCl$_3$ 300 MHZ): δ 0.92(t 24H), δ 1.30–1.50 (mm 32H), δ 3.10 (t 16H), 6 8.00 (m 4H). Melting point 135–137° C.

Example 13

Synthesis of mono-hydroxyethyl terephthalate (MHET)

The synthesis of MHET was performed by the esterification of terephthalic acid (TA) with ethylene oxide (EO), in the presence of a supercritical fluid (SCF) and in the presence of an esterification catalyst as follows:

Prior to reaction dimethyl ether and ethylene oxide were added to a high pressure syringe pump (ISCO 500D). The pump was pressurized to 70 bar with 200 ml of fluid. Ethylene oxide was then metered in as a liquid (0.5 mole % with respect to the SCF) with a pressure generator (High Pressure Products Model #62-2-10). Sufficient DME was subsequently added through the same port in order to flush all the ethylene oxide into the pump cylinder and to improve mixing. The contents were then thoroughly mixed by coupling an external magnet with a Teflon coated magnetic stir bar (Fisher Scientific) previously placed in the pump. Mixing was verified by performing multiple runs with identical conditions from the same pump mixture.

The catalyst/terephthalic acid solid mixture was prepared by adding 10 grams of terephthalic acid (from Amoco Chemicals), EHPB catalyst (5 mol % with respect to terephthalic acid), and sufficient volume of methylene chloride to dissolve all the catalyst (~100 ml). The mixture was shaken in a round bottom flask and the methylene chloride was removed by rotary evaporation to ensure a uniform coating of the terephthalic acid with catalyst. 0.2 grams of the terephthalic acid/catalyst mixture was then loaded into the 0.250" diameter reaction thimble insert and held in place with glass wool. The thimbles were placed in a desiccator until required for reaction.

The reactions were performed in an HP 7680T supercritical fluid extractor modified to accept a variety of solvents. The dimethyl ether/ethylene oxide mixture was mixed at room temperature and pumped at 70 bar at a flowrate of 5 ml/min. The mixture was heated to the reaction temperature prior to entering the reaction zone and the dimethyl ether/ethylene oxide mixture was pumped over the terephthalic acid/catalyst reaction mixture for 15 minutes. The reaction products were carried out of the reaction zone with the supercritical fluid and collected in a trap during depressurization. The trap was rinsed with acetone containing standard anthracene at a concentration of 0.5 mg/ml. The solution was then analyzed by GC-FID.

The reaction was repeated using EHPI, EHPC, EHPT, BPC, BVDC, XPDC, TBTA, CBCP, NBPC, NPC MPC and NBPB as catalysts.

In each of the above performed runs, the final product was identified as mono-hydroxyethyl terephthalate (MHET).

What is claimed is:

1. A compound represented by the formula wherein X is selected from a group consisting of halogen, alkoxide, aryloxide, cyanide, thiocyanide, acetate, nitrate or a counterion with a nucleophilicty of greater than 1 as calculated from the Swain-Scott equation, $R_1$ and $R_2$ may be the same or different and are selected from hydrogen or $C_1$–$C_{10}$ alkyl;

$R_3$ is selected from a group represented by the formula wherein, Z is selected from a group consisting of halogen, nitro, alkoxy or a group represented, nitro, alkoxy and groups represented by the formula wherein $R_1$ and $R_2$ and X are defined above.

2. A compound as claimed in claim 1, wherein said compound is selected from the group consisting of N-p-chlorobenzyl-(N,N-dimethylamino)pyridinium chloride (CBPC), N-p-nitrobenzyl(N,N-dimethylamino)pyridinium chloride (NBPC), N-p-nitrobenzyl(N,N-dimethylamino) pyridinium bromide (NBPB), N-p-methoxybenzyl(N,N-dimethylamino)pyridinium chloride (MBPC), and Xylyl-bis N,N,-(N,N,-dimethylaminopyridinium) dichloride (XPDC).

* * * * *